United States Patent [19]

Hopkins

[11] Patent Number: 4,485,016

[45] Date of Patent: Nov. 27, 1984

[54] ENZYMATIC REMOVAL OF AROMATIC HYDROXY COMPOUNDS AND AROMATIC AMINES FROM WASTE WATERS

[75] Inventor: Thomas R. Hopkins, Bartlesville, Okla.

[73] Assignee: Phillips Petroleum Company, Bartlesville, Okla.

[21] Appl. No.: 595,142

[22] Filed: Mar. 30, 1984

Related U.S. Application Data

[63] Continuation-in-part of Ser. No. 494,489, May 13, 1983, abandoned.

[51] Int. Cl.³ .............................................. C02F 1/74
[52] U.S. Cl. .................... 210/632; 210/717; 210/721; 210/759; 210/909; 435/262
[58] Field of Search ............... 210/632, 606, 909, 759, 210/763, 721, 724, 717; 435/14, 25, 28, 262, 264, 188

[56] References Cited

U.S. PATENT DOCUMENTS

| | | | |
|---|---|---|---|
| 4,247,641 | 1/1981 | Neidleman et al. | 435/123 |
| 4,250,261 | 2/1981 | Eggeling et al. | 435/190 |
| 4,271,264 | 6/1981 | Modrovich | 435/14 |
| 4,370,199 | 1/1983 | Orndorff | 210/764 |

FOREIGN PATENT DOCUMENTS 69-2200  3/1969  South Africa .
914508   3/1982  U.S.S.R. .............................. 210/759

OTHER PUBLICATIONS

Klibanov et al.; "Enzymatic Removal of Toxic Phenols and Anilines from Waste Waters"; *Jour. of Applied Biochem.* 2; pp. 414–421 (1980).
Klibanov et al.; "Horseradish Peroxidase for the Removal of Carcinogenic Aromatic Amines from Water"; *Enzyme Microb. Technology* 3; pp. 119–122 (1981).
1981 A.C.S. Annual Meeting; *C&EN* p. 53 (Sep. 14, 1981); "Horseradish Peroxidase Cleans Up Wastewater.
Wesley; "Glucose Oxidase Treatment Prolongs Shelf Life of Fresh Seafood;" *Food Development*, Jan. 1982; pp. 36–38.

*Primary Examiner*—Benoit Castel

[57] ABSTRACT

A process for the removal of at least one compound selected from the group consisting of an aromatic hydroxy compound or an aromatic amine having a water solubility of at least 0.01 mg/L from waste water containing the same, which comprises treating the water with a treating agent which consists essentially of peroxidase, at least one agent selected from the group consisting of alcohol oxidase and a straight chain $C_1$ to $C_4$ alcohol or glucose oxidase and glucose and an azide salt of the formula $MN_3$.

14 Claims, No Drawings

ENZYMATIC REMOVAL OF AROMATIC HYDROXY COMPOUNDS AND AROMATIC AMINES FROM WASTE WATERS

This application is a continuation-in-part of U.S. Ser. No. 494,489, filed May 13, 1983 now abandoned.

This invention relates to a novel stabilized enzyme reagent and the use of enzyme reagent systems in the removal of aromatic hydroxy compounds and/or aromatic amines from waste waters.

Aromatic hydroxy compounds and aromatic amines are commonly present in waste waters of a number of industries. Such aromatic hydroxy compounds and aromatic amines can be toxic when present in elevated levels. In addition, aromatic hydroxy compounds and aromatic amines also have a relatively high biological oxygen demand and therefore when present in sufficient concentrations can greatly reduce or deplete the oxygen in a body of water containing them.

Conventional processes for removal of aromatic hydroxy compounds and aromatic amines from industrial waste waters include extraction, adsorption on activated carbon, steam distillation, bacterial and chemical reaction (oxidation), electrochemical techniques and irradiation. All of these methods, although certainly feasible and useful, suffer from serious drawbacks, e.g., high cost, incompleteness of purification, formation of hazardous by-products or low efficiency. This situation has necessitated a search for alternative methods.

Recently as disclosed in the *Journal of Applied Biochemistry* 2, pp 414–421 (1980), phenols and anilines present in waste water could be removed by the addition of peroxidase and hydrogen peroxide to the waste water, thereby causing the precipitation of phenols and aromatic amines from the water in the form of insoluble, apparently non-toxic polymers.

The above system, although effective for its intended purpose, has serious shortcomings which preclude it from being commercially attractive. Namely, hydrogen peroxide is expensive, unstable on storage and short lived in a real waste stream situation where metal salts, sunlight, and bacteria break it down rather quickly to oxygen and water. Thus a method which would avoid problems previously experienced is highly desirable.

It is an object of this invention to provide an improved process for the removal of aromatic hydroxy compounds or aromatic amines from waste streams.

Another object of this invention is to provide a novel enzyme reagent system for treatment of waste streams.

Other aspects, objects, and advantages of the present invention will become apparent from this specification and claims.

In accordance with the present invention, I have discovered that water soluble aromatic hydroxy compounds and/or aromatic amines may be efficiently and economically removed from bodies of water containing the same by treating the water with a treating agent which consists essentially of peroxidase and at least one enzyme reagent selected from the group consisting of alcohol oxidase and a straight chain $C_1$ to $C_4$ alcohol or glucose oxidase and glucose.

By treating the water in this manner, $H_2O_2$ is produced continuously in situ thereby avoiding the problem of $H_2O_2$ storage instability. Also, a constant source of $H_2O_2$ is provided by the reaction of alcohol oxidase or glucose oxidase, their individual substrate, and oxygen.

In addition, I have discovered that by admixing peroxidase and alcohol oxidase or glucose oxidase and an azide salt of the formula $MN_3$ there is formed a novel enzyme reagent system which can be conveniently utilized in the process of this invention and which is readily activated upon the addition of an appropriate substrate, i.e., a straight chain $C_1$ to $C_4$ alcohol or glucose.

In the present invention, the term aromatic hydroxy compound is defined as being one wherein an OH group is attache to an aromatic or substituted aromatic nucleus. The aromatic nucleus may be either a monoaromatic compound such as phenol or a polynuclear aromatic compound such as 2-naphthol. Examples of suitable substituent groups on the aromatic nucleus include OH, SH, OR, SR, RSO, $RSO_2$, wherein R is a $C_1$ to $C_{20}$ hydrocarbyl radical, $C_1$ to $C_{20}$ hydrocarbyl radicals themselves, halogens, $SO_3M$ wherein M is hydrogen or a Group IA metal, amides, amines, carboxylic acid and cyano functionalities.

Representative examples of such aromatic hydroxy compounds include phenol, guaiacol, cresol, resorcinol, chlorophenols, aminophenols, 2',7'-dichlorofluorescein, 5,7-dichloro-8-hydroxyquinoline, 1,8-dihydroxyanthraquinone, 2,4-dihydroxy-5,6-dimethylpyrimidine, 4,6-dihydroxy-2-mercaptopyrimidine, 3,6-dihydroxypyridazine, 4,8-dihydroxyquinoline-2-carboxylic acid, 2,3-dihydroxyquinoxaline, 1,5-dihydroxy-1,2,3,4-tetrahydronaphthalene, 2-(dimethylaminomethyl)-3-hydroxypyridine, 1-naphthol, 1,3-naphthalenediol, 1,2-nitroso-1-naphthol, 2,7-naphthalenediol, p-phenylphenol, 5-indanol, and 8-hydroxyquinoline.

As used in this invention, the term aromatic amine is defined to be one wherein a primary amine group is attached to an aromatic or substituted aromatic nucleus. The aromatic nucleus may be either monoaromatic as in the case of aniline or polynuclear as in the case of 1-aminonaphthalene. Examples of possible substitution groups on the aromatic nucleus are the same as given earlier for the aromatic hydroxy compounds.

Representative examples of such aromatic amines include aniline, benzidine, 4-chloroaniline, 4-bromoaniline, 4-fluoroaniline, 4-bromo-2-methylaniline, m-phenylenediamine, N(1-naphthyl)ethylenediamine, 1-aminonaphthalene, 2-aminonaphthalene, ethidium bromide, 6-hydroxy-2,4,5-triaminopyrimidine sulfate, N'-(6-indazolyl)sulfanilamide, 5'-iodo-5'-deoxyadenosine, o-dianisidine, 3,3'-diaminobenzidine, 3,3'-dichlorobenzidine, o-tolidine, p-phenylazoaniline, 4-aminophenol, 1-naphthylamine, 2-naphthylamine, and 5-nitro-1-naphthylamine.

The aromatic hydroxy compounds or aromatic amine compounds which are removed by the process of this invention must have generally a solubility in water of at least about 0.01 mg/liter, and preferably at least about 0.05 mg/liter.

Peroxidase, alcohol oxidase, and glucose oxidase enzymes are commercially available from biological supply houses such as Sigma Chemical Company, St. Louis.

Preferably the alcohol oxidase utilized in this invention is purified from *Pichia pastoris* which is known to have low sensitivity to $H_2O_2$. The purified alcohol oxidase employed is preferably essentially free of catalase activity.

A suitable glucose oxidase utilized in this invention is purified from *Aspergillus niger*.

Suitable sources of peroxidase enzyme are purified from, plant, animal and microbial sources. Included are horseradish peroxidase, turnip peroxidase, seaweed peroxidase, chloroperoxidases such as isolated from *Caldariomyces fumago* and lactoperoxidases such as isolated from mammalian milk.

The alcohol substrates useful in the present invention are the straight chain $C_1$ to $C_4$ alcohols. Most commonly used are methanol and ethanol and most preferred is methanol.

Suitable substrates for glucose oxidase include $\beta$-D-glucose, also known as dextrose.

In addition, the glucose oxidase substrate can be indirectly provided to the reaction mixture by employing a precursor carbohydrate in combination with an appropriate hydrolase enzyme. For example, starch can be hydrolyzed to glucose in the presence of amylase and glucoamylase; sucrose can be converted to a mixture of glucose and fructose in the presence of invertase; lactose can be converted to glucose and galactose in the presence of lactase; cellulose can be converted to glucose in the presence of cellulase.

The reagent system which is useful in carrying out the process of this invention consist essentially of a mixture of the enzymes alcohol oxidase or glucose oxidase and peroxidase and an azide of the formula $MN_3$ wherein M is $NH_4^+$ or an alkali metal compound. The azide functions as an enzyme stabilizer.

Such a system can be of any size with the only limitation being that the components be present in the following ranges:

| | |
|---|---|
| Alcohol oxidase | 10 to 1,000 units/mL, |
| Glucose oxidase | 10 to 1,000 units/mL, |
| Peroxidase | 10 to 10,000 ppg units/mL, |
| $NaN_3$ | .01 to 0.5 weight percent | and wherein the ratio of AO to POD, units is 10:1 to 1:10, preferably 1 Unit AO:1 Unit POD.

While the novel enzyme reagent system of this invention provide a convenient means for carrying out the waste water treatment, the individual reagent components can also be added separately to the waste water. The order of addition of the individual components or the reagent system to the waste water to be treated is not critical so long as a suitable substrate is provided to the reaction mixture at the time of addition of the reagent system or the individual enzymes.

The amount of peroxidase and oxidase enzymes added to the body of water is not generally dependent upon the concentration of aromatic hydroxy compound or aromatic amine present. The more critical variable appears to be the amount of oxidase enzyme substrate employed, since the amount of $H_2O_2$ which can ultimately be generated will be limited by the amount of substrate provided. Thus, the greater the concentration of aromatic hydroxy compound or aromatic amine in the solution to be treated, the greater amount of oxidase substrate will preferably be employed. In general sufficient reagents are added to generate an excess of $H_2O_2$. The order of addition of these reagents to the reaction mixture is not thought to be critical in the present invention.

The following Table sets forth the ranges of reagents per liter of waste water which are believed useful:

TABLE I

| Reagent | Concentration | |
|---|---|---|
| | Broad | Preferred |
| Oxidase Substrate | 5–10,000 mg/L | 25–750 mg/L |
| Oxidase Enzyme | 0.1–10,000 U/L | 10–1000 U/L |
| Peroxidase | 0.1–10,000 U/L | 10–1000 U/L |

An oxidase enzyme unit (U) is described as that quantity of enzyme which catalyzes the transformation of 1 $\mu$mole (micro mole) of substrate per minute under standard conditions.

Peroxidase activity is expressed in purpurogallin units (ppg U) which is defined as the amount of enzyme that will oxidize one milligram of pyrogallol to purpurogallin in 20 seconds at 20° C. in the presence of hydrogen peroxide.

Whatever concentration of reagents are employed should be in an amount sufficient to effectively remove all or essentially all of the aromatic hydroxy compounds and/or aromatic amines present.

In a presently preferred embodiment of the present invention, sodium azide is added to a concentrated stock solution of peroxidase and either alcohol oxidase or glucose oxidase to form a novel stabilized reagent concentrate. The azide ion serves to stabilize the enzyme by physical interaction with the proteins of the enzymes by forming a competitive inhibitor-enzyme complex. Therefore, it is contemplated that the use of sodium azide in the present invention will operate to stabilize the combination of peroxidase and either alcohol oxidase or glucose oxidase enzymes. Generally, the azide salt ($NaN_3$) in the concentrated stock solution will be present in an amount from about 100 to over 500 mg/L, preferably about 200 mg/L (per liter of mixed enzymes). Upon addition of the concentrated enzyme, azide salt stock solution to the waste water, the azide salt is greatly diluted out and is no longer bacteriostatic or inhibitory to the enzymes.

The reaction temperature should be from about 0° C. to about 50° C., preferably about 20° C. to 45° C.

The reaction should be conducted at a pH in the range of about 4–11 and preferably about 6–10.

The reaction or treatment time will be from about 5 min. to about 48 hours.

In carrying out the process of the present invention, the waste water should be aerated. This can be achieved by stirring or bubbling air through the solution.

At the end of the reaction time, the precipitated aromatic hydroxy compounds and aromatic amines may be separated from the water containing them by such conventional techniques as filtration, centrifugation, sedimentation, flotation and the like. Since the polymerized end products appear to be non-toxic, they may also be left in the treated stream.

Immobilized enzymes are also operable in the practice of the present invention. Thus, peroxidase and an oxidase enzyme can be immobilized and loaded into a flow reactor through which the fluid to be treated is then passed. Such a mode of operation has the benefit of allowing continuous wastewater treatment and reuse of the enzymes.

The following examples further illustrate the present invention.

EXAMPLE I

Alcohol Oxidase Preparation and Purification

In a continuous aerobic fermentation process, methanol and an aqueous mineral salts medium in a volume ratio of about 40 to 60, respectively, were fed individually to a fermentor, inoculated with the yeast species *Pichia pastoris* NRRL Y-11430, at a rate so that methanol is the growth-limiting factor. The fermenter was a 1500-liter foam-filled fermenter with a liquid volume of about 610 liters, with automatic pH, temperature, and level control. Agitation was provided by two conventional paddle-type turbines driven at 1000 rpm. The aeration rate was about 4 volumes of air (at about 38 psig and about 25° C.) per volume of ferment in the fermenter per minute. Anhydrous ammonia was added at such a rate as to maintain the pH of the fermentation mixture at about 3.5.

The aqueous mineral salts medium was prepared by mixing, with each liter of tap water, 15.86 mL 75 percent $H_3PO_4$, 9.53 g $K_2SO_4$, 7.8 g $MgSO_4.7H_2O$, 0.6 g $CaCl_2.2H_2O$, and 2.6 g 85 percent KOH. The trace mineral solution plus biotin was fed separately via the methanol stream at a rate of 10 mL per liter of methanol. The trace mineral solution plus biotin was prepared by mixing 780 mL of a trace mineral solution, 20 mL water, 200 mL methanol and 0.032 g biotin.

The trace mineral solution was prepared by mixing, for each liter of solution, 65 g $FeSO_4.7H_2O$, 20 g $ZnSO_4.7H_2O$, 3.0 g $MnSO_4.H_2O$, 6.0 g $CuSO_4.5H_2O$, 5.0 mL conc. $H_2SO_4$, and sufficient deionized water to make 1 liter of solution.

The aqueous mineral salts medium was fed at a rate of 31.5 liters per hour and the methanol at a rate of 21 liters per hour.

The fermentation was conducted at about 30° C. and about 38 psig pressure, with a fermentation time of 11.6 hours.

For analytical purposes, the resulting yeast cells were separated from the fermentation effluent (ferment) by centrifugation, washed by suspension in water and recentrifugation, dried overnight at 100° C., and weighed. On a dried basis, the yield of yeast cells typically was about 40.6 g per 100 g of methanol fed. The cell density typically was about 128.4 g of cells per liter of fermenter effluent. The total solids content of the ferment typically was about 134.7 g per liter, cells plus dissolved solids. A portion of the fermenter effluent was frozen and stored.

Fermentation of *Pichia pastoris* NRRL Y-11430 was carried out by a method of which that set forth above is typical. A portion of the fermenter effluent was removed and adjusted to pH 7.5 with ammonium hydroxide, and was homogenized on a Dyno-Mill ® Model KDL using a 0.6 liter vessel in a continuous operation at 30° C. using belt combination #3 and a flow of 20–30 mL/hr. The beads in the mill were lead-free glass beads with a diameter of 0.3–0.5 mm. The resulting homogenate was centrifuged at 5° C. and 20,000×g for 30 minutes to yield a cell-free supernatant. The cell-free supernatant enzyme activity measured by the dye-peroxidase method described below was about 330 EU/mL. The supernatant was stored frozen for future use. This describes the preparation of crude yeast homogenate.

Six 130 mL portions of the supernatant were placed in cellulose acetate dialysis bags and dialyzed at 5° C. against about 8 liters of distilled water. After 4 days, the aqueous phase of each bag was decanted. The solids remaining in the bags consisted of two types of solid. The thin upper white layer was carefully removed and discarded. The bottom solid was brown-yellow and was crystalline alcohol oxidase. A portion of the crystalline alcohol oxidase was dissolved in distilled water (about 10 times the volume of the solid) and an assay by the dye-peroxidase method described below showed an activity of 94 EU/mL. The specific activity of the alcohol oxidase was 10.4 EU/mg of protein.

A sample of the solid alcohol oxidase was examined by SDS gel electrophoresis and a single band was observed indicating a homogeneously pure enzyme. A comparison of electrophoretic mobility with those of proteins having known molecular weight indicates a subunit molecular weight of about 72,000±3000 (estimated). This describes the preparation of pure yeast alcohol oxidase from *Pichia pastoris*.

The alcohol oxidase activity for reaction with methanol was determined by the dye-peroxidase method. A dye-buffer mixture was prepared by mixing 0.1 mL of an o-dianisidine solution (1 weight percent o-dianisidine in water) with 12 mL of aerated 0.1M sodium phosphate buffer (pH 7.5). The assay mixture was prepared with 2.5 mL of the dye-buffer mixture, 50 μL of methanol, 10 μL of a peroxidase solution (1 mg of horse-radish peroxidase-Sigma, Type II), and 25 μL of the alcohol oxidase solution. The assay mixture was maintained at 25° C. in a 4×1×1 cm cuvette and the increase in absorbance by the dye at 460 nm was recorded for 2 to 4 minutes. The enzyme activity was calculated by $$\text{Activity } (\mu \text{ mole/min/mL or Enzyme Units/mL}) = \frac{\Delta A}{\text{min.}} \times 11.5$$

wherein 11.5 is a factor based on a standard curve prepared with known aliquots of $H_2O_2$ and $\Delta A$ is the change in absorbance during the experimental interval.

In the following examples, artificial waste water systems were prepared by addition of 10 microliters of saturated phenol or guaiacol (2-methoxyphenol) to an aqueous buffered solution. Buffered solutions were employed to eliminate variables pH which otherwise is experienced in most water sources.

EXAMPLE II

The prior art treatment of water containing phenols was repeated as follows. A series of 250 mL beakers were charged with 100 mL of 50 mM sodium acetate buffer (pH 3.5 or 5.5) or 100 mL of 10 mM potassium phosphate buffer (pH 7.5), 1 mL of horseradish peroxidase (10 U/mL), 10 μL of water-saturated phenol or guaiacol (2-methoxyphenol) and 10 μL of 30% aqueous $H_2O_2$. Each mixture was incubated at room temperature for 3 hours without stirring. Phenol removal was determined by gas liquid chromatography (glc).

| Sample | Phenol Employed | pH | Phenol Removal |
| --- | --- | --- | --- |
| 1 | Phenol | 3.5 | 52% |
| 2 | Guaiacol | 5.5 | 100% |
| 3 | Guaiacol | 7.5 | 93% |

Two similar mixtures were prepared in 1000 mL beakers employing alcohol oxidase plus alcohol in place of the $H_2O_2$. 100 mL of 50 mM potassium phosphate buffer (pH 7.5), 1 mL of horseradish peroxidase (10 U/mL), 10 μL of guaiacol, 100 μL of alcohol oxidase (AO) solution (1000 U/mL) and 100 μL of methanol in one beaker and ethanol in the other were mixed, and each then stirred for 3 hours at room temperature. Phenol removal was determined as above. Guaiacol removal after three hours was essentially quantitative (~100%) when either methanol or ethanol was employed.

The results of these experiments demonstrate that the inventive waste water treatment process is at least as effective as prior art enzymatic treatment processes.

EXAMPLE III

The effect of alcohol oxidase concentration on the percent removal of aromatic hydroxy compound was studied. A series of standard mixtures containing 100 mL of 50 mM potassium phosphate buffer (pH 7.5), 1 mL of peroxidase (10 U/mL), 10 μL of either phenol (water saturated) or guaiacol, and 100 μL of methanol in a 1000 mL beaker were each treated with aliquots of alcohol oxidase (1000 U/mL total), then stirred at room temperature for 3 hours before being analyzed by glc for phenol or guaiacol removal.

| Sample | μL added AO | % Removal Guaiacol | Phenol |
|---|---|---|---|
| 1 | 0 | 0 | |
| 2 | 1 | 89.5 | |
| 3 | 5 | 98.6 | |
| 4 | 25 | 98.6 | |
| 5 | 100 | — | |
| 6 | 0 | | 0 |
| 7 | 1 | | 83 |
| 8 | 5 | | 88 |
| 9 | 25 | | 96 |
| 10 | 100 | | 99.8 |

The results of these experiments demonstrate the effectiveness of the inventive process for the removal of aromatic hydroxy compounds such as guaiacol and phenol from an aqueous solution. Excellent aromatic hydroxy compound removal is achieved even with very low levels of alcohol oxidase (~1U AO/100 mL of solution).

EXAMPLE IV

The rate of aromatic hydroxy compound removal from an aqueous solution was studied by following the disappearance of guaiacol as a function of time for the following reagent mixture:
10 μL guaiacol
100 mL 50 mM potassium phosphate buffer (pH 7.5)
1 mL horseradish peroxidase (100 U/mL)
5 μL alcohol oxidase (1000 U/mL)
100 μL methanol This mixture was stirred in a 1000 mL beaker at room temperature, and a series of samples taken from time to time were monitored by glc for guaiacol disappearance.

| Sample | Lapsed Time, hr | % Guaiacol Removal |
|---|---|---|
| 1 | 0 | 0 |
| 2 | 0.2 | 51 |
| 3 | 0.4 | 77 |
| 4 | 1 | 98.3 |
| 5 | 2 | 98.3 |

The results of this experiment demonstrate that aromatic hydroxy compound removal by the inventive method is quite rapid—over half of the guaiacol having been removed in only 12 minutes (Sample 2), with essentially complete guaiacol removal after only one hour (Sample 4).

EXAMPLE V

The effect of pH of the efficacy of the inventive waste water cleanup system was investigated over a wide pH range. A series of 1000 mL beakers were charged with:
10 μL of water saturated phenol
100 μL of methanol
200 μL of alcohol oxidase (1000 U/mL)
1 mL horseradish peroxidase (100 U/mL) and either:
100 mL of 50 mM sodium acetate buffer (pH 4–6) or
100 mL of 50 mM potassium phosphate buffer (pH 7–11)

Each mixture was stirred at room temperature for three hours and then monitored by glc for phenol removal.

| Sample | pH | % Phenol Removal |
|---|---|---|
| 1 | 4 | 19 |
| 2 | 5 | 61 |
| 3 | 6 | 95.4 |
| 4 | 7 | 95.4 |
| 5 | 8 | 98.6 |
| 6 | 9 | 99.1 |
| 7 | 10 | 98.9 |
| 8 | 11 | 26.6 |

The results of this experiment demonstrate that the inventive waste water treatment process is effective over the pH range of 4–11. Particularly good results are obtained in the pH range of 6–10. At a pH of 10, it was also observed that the solids formed in the presence of peroxidase, methanol and alcohol oxidase aggregated to the largest particle size thus indicating the preferred pH where solids removal would also be desired.

EXAMPLE VI

The effect of methanol concentration on the degree of aromatic hydroxy compound removal was studied by adding various amounts of methanol to a series of 1000 mL beakers containing:
100 mL 50 mM potassium phosphate buffer (pH 7.5)
1 mL horseradish peroxidase (100 U/mL)
200 μL alcohol oxidase (1000 U/mL)
10 μL guaiacol The resulting mixture was stirred at room temperature for three hours, and then monitored by glc for guaiacol removal.

| Sample | Added Methanol, μL | % Guaiacol Removal |
|---|---|---|
| 1 | 0 | 0 |
| 2 | 1 | 60 |
| 3 | 5 | 97.9 |
| 4 | 25 | 98.6 |
| 5 | 100 | 99.2 |

The procedure employed above was then repeated, except only 10 μL of alcohol oxidase were used.

| Sample | Added Methanol, μL | % Guaiacol Removal |
|---|---|---|
| 6 | 0 | 0 |
| 7 | 1 | 47 |
| 8 | 5 | 98.4 |

-continued

| Sample | Added Methanol, μL | % Guaiacol Removal |
| --- | --- | --- |
| 9 | 25 | 99.3 |
| 10 | 100 | 99.5 |

The results of these experiments indicate that effective aromatic hydroxy compounds removal is achieved with the inventive waste water treatment process with very low levels of alcohol such as methanol present. Thus, greater than 98% guaiacol removal was observed when only 10 μL of alcohol oxidase and 5 μL of methanol were added to 100 mL of water containing a phenolic compound.

EXAMPLE VII

The effect of peroxidase concentration on the efficiency of aromatic hydroxy compound removal was studied. A series of 1000 mL beakers were charged with 100 mL 50 mM potassium phosphate buffer (pH 7.5), 10 μL of alcohol oxidase (1000 U/mL), 10 μL of methanol, (Samples 1-14), 10 μL of guaiacol (Samples 1-9), or phenol, (Samples 10-18), and 0-1 mL of peroxidase (100 U/mL). The mixtures were stirred at room temperature for three hours, then monitored by glc for disappearance of aromatic hydroxy compound.

| | μL Added | % Aromatic Hydroxy Compound Removal | |
| --- | --- | --- | --- |
| Sample | Horseradish Peroxidase | Guaiacol | Phenol |
| 1 | 0 | 0 | |
| 2 | 1 | 8 | |
| 3 | 5 | 15 | |
| 4 | 25 | 73 | |
| 5 | 50 | 96.7 | |
| 6 | 100 | 97.6 | |
| 7 | 200 | 99.6 | |
| 8 | 500 | 99.6 | |
| 9 | 1000 | 100 | |
| 10 | 0 | | 0 |
| 11 | 1 | | 4 |
| 12 | 5 | | 0 |
| 13 | 25 | | 16 |
| 14 | 50 | | — |
| 15 | 100 | | 24.4 |
| 16 | 200 | | 59 |
| 17 | 5000 | | 83 |
| 18 | 1000 | | 99.9 |

In Samples 15-18, 100 μL methanol was employed because rather than 10 μL as in Samples 1-14 to assure adequate in situ generation of sufficient H$_2$O$_2$ to effect removal of the added hydroxy compound.

The results of these experiments demonstrate that effective aromatic hydroxy compound removal can be achieved employing very low levels of horseradish peroxidase—as low as 25 μL per 100 mL of aromatic hydroxy compounds containing solution. Excellent results are obtained employing about 100 U/L of horseradish peroxidase for guaiacol removal and about 1000 U/L of horseradish peroxidase for phenol removal.

EXAMPLE VIII

The applicability of the inventive waste water treatment method to 1-naphthol and benzidine was studied. A series of 1000 mL beakers were charged with 100 mL of 50 mM potassium phosphate buffer (pH 7.5), 100 μL of methanol containing 10 mg of 1-naphthol or benzidine, and amounts of horseradish peroxidase solution (100 U/mL) and alcohol oxidase solution (1000 U/mL) as indicated below. Each beaker was stirred at room temperature for seven hours. 1-Naphthol removal was monitored by glc, benzidine removal was monitored by measuring the absorbancy at 280 nm of the sample and comparing to a standard curve.

| | | % Removal | |
| --- | --- | --- | --- |
| Sample | μL Peroxidase Added | 1-Naphthol | Benzidine |
| A. 100 μL AO | | | |
| 1 | 0 | 0 | |
| 2 | 1 | 0 | |
| 3 | 2 | 5.5 | |
| 4 | 5 | 11.4 | |
| 5 | 10 | 19.0 | |
| 6 | 25 | 39.8 | |
| 7 | 50 | 58.6 | |
| 8 | 100 | 83.6 | |
| 9 | 0 | | 0 |
| 10 | 1 | | 0 |
| 11 | 2 | | 36 |
| 12 | 5 | | 10 |
| 13 | 10 | | 45 |
| 14 | 25 | | 65 |
| 15 | 50 | | 71 |
| 16 | 100 | | 100 |
| B. 10 μL AO | | | |
| 17 | 0 | 0 | |
| 18 | 25 | 12 | |
| 19 | 50 | 36 | |
| 20 | 100 | 58.8 | |
| 21 | 250 | 100 | |
| 22 | 0 | | 0 |
| 23 | 25 | | 20.1 |
| 24 | 50 | | 27.4 |
| 25 | 100 | | 58.0 |
| 26 | 250 | | 100 |

The results of these experiments demonstrate that the inventive waste water treatment process is effective for removing a variety of compounds from water, such as 1-naphthol and benzidine. In addition, it is shown that alcohol oxidase levels as low as 10 μL/100 mL (or about 10 units of enzyme per liter of water to be treated) and peroxidase levels as low as about 50 μL/100 mL (or about 50 enzyme units per liter of water to be treated) can be employed.

EXAMPLE IX

The rate of benzidine removal from an aqueous solution was studied by measuring the disappearance of benzidine from a solution containing:
100 mL 50 mM potassium phosphate buffer (pH 7.5)
100 μL alcohol oxidase (1000 U/mL)
100 μL horseradish peroxidase (100 U/mL)
100 μL methanol
10 mg benzidine The solution was stirred at room temperature in a 1000 mL beaker. Periodically samples were withdrawn for a UV to determination of the amount of benzidine removal accomplished.

| Sample | Lapsed Time, minutes | % Benzidine Removal |
| --- | --- | --- |
| 1 | 0 | 0 |
| 2 | 5 | 74 |
| 3 | 30 | 94.7 |
| 4 | 60 | 96.1 |
| 5 | 180 | 97.1 |

The results of these experiments demonstrate that a substantial amount of an aromatic amine compound such as benzidine is rapidly removed by the inventive waste water treatment process, i.e. greater than 70% removal is only 5 minutes.

EXAMPLE X

The effect of added methanol and formaldehyde on the efficiency of the prior art waste treatment process employing horseradish peroxidase plus $H_2O_2$ was studied. A series of 1000 mL beakers were charged with 100 mL of 50 mM potassium phosphate buffer (pH 7.5), 1 mL horseradish peroxidase (100 U/mL), 10 μL phenol and various additives as indicated below. The solutions were stirred at room temperature for three hours, then assayed by glc for disappearance of phenol.

| Sample | Additive(s) | % Phenol Removal |
|---|---|---|
| 1 | 10 μL $H_2O_2$ (30%) | 41.4 |
| 2 | (1) + 300 μL HCHO (37%) | 37.2 |
| 3 | (1) + 100 μL MeOH | 52.7 |
| 4* | 100 μL MeOH + 10 μL AO (1000 U/mL) | 61.1 |
| 5** | 10 μL $H_2O_2$ | 0 |

*$H_2O_2$ omitted from this sample
**Peroxidase omitted from this sample

Sample 4 indicates that the addition of methanol and alcohol oxidase, thereby resulting in the in situ production of $H_2O_2$, resulted in the highest removal of phenol. Sample 1 corresponds to the prior art treatment of waste water wherein $H_2O_2$ is added directly. Samples 2 and 3 show that the mere addition of formaldehyde and methanol in combination with $H_2O_2$ to the waste water treatment process can result in detrimental effects (Sample 2) or beneficial effects (Sample 3) which, however, is still below the results achieved by the process of the present invention (Sample 4).

EXAMPLE XI

Additional experiments were carried out to determine the effect of added methanol and formaldehyde on the prior art waste water treatment process. Thus, a series of 1000 mL beakers containing 100 mL 10 mM potassium phosphate buffer (pH 7.0), 10 μL phenol, 100 μL horseradish peroxidase, and additional reagents as indicated below were prepared at room temperature for three hours and then assayed by glc for disappearance of phenol.

| Sample | Additive(s) | % Phenol Removal |
|---|---|---|
| 1* | None | 0 |
| 2 | 10 μL $H_2O_2$ (30%) | 52 |
| 3 | (2) + 15 μL HCHO (37%) | 49 |
| 4 | (2) + 100 μL MeOH | 53 |
| 5 | (2) + 15 μL HCHO + 100 mL MeOH | 43 |
| 6 | 10 μL AO (1000 U/mL) + 100 μL MeOH | 58 |

*Peroxidase omitted from this sample

Sample 2 corresponds to the prior art waste water treatment process. As seen in Example X, addition of formaldehyde appears to have a small detrimental effect on the efficiency of the process, and addition of methanol appears to have a small beneficial effect on the efficiency of the process. Sample 5, however, demonstrates that simply adding methanol and formaldehyde has a negative effect on the prior art treatment process. Compare this to Sample 6 where methanol and alcohol oxidase are added, thereby leading to the production of HCHO and $H_2O_2$ in the reaction mixture. The % phenol removal observed is higher than that achieved with any of the reagent combinations with the prior art system.

EXAMPLE XII

A suitable reagent pack for use in the inventive waste water treatment process will preferably include the presence of an enzyme stabilizer. The following experiment was carried out to demonstrate that an azide salt such as $NaN_3$ could be employed to preserve an alcohol oxidase/horseradish peroxidase enzyme combination without irreversibly inhibiting the enzymes. The dye-peroxidase assay procedure described in Example I was carried out on two samples, one containing 0.02 wt. % $NaN_3$ and the control sample containing no $NaN_3$. After a 100 fold dilution in water, the activity for the two diluted samples was essentially the same (61.9 U/mL in the presence of $NaN_3$, 62.1 U/mL absent $NaN_3$).

This experiment demonstrates that sodium azide inhibition is reversible for the enzyme combination alcohol oxidase/peroxidase.

EXAMPLE XIII

The inventive waste water treatment process was compared to a bacterial process for phenol removal. Four reactor cells (300 mL) were charged with 100 mL of solution containing 35 mg/L of phenol. These cells were further treated as follows:

(1) Vigorous air sparging only;
(2) Peroxidase, alcohol oxidase, methanol and vigorous air sparging,
(3) As in (2) plus an inoculum of bacteria acclimated to a continuous feed of 3.5 mg/L of phenol;
(4) An inoculum of bacteria as employed in (3) with vigorous air sparging.

The peroxidase and alcohol oxidase were added in (2) and (3) at the rate of 1 mL of a stabilized enzyme solution (comprising 1000 U of alcohol oxidase, 1000 U of horseradish peroxidase, and 2 mg of $NaN_3$ in 10 mL of 50 mM potassium phosphate buffer (pH 7.5)) per liter of solution to be treated. Methanol was added separately at the rate of 0.1 mL/L of solution to be treated.

The four samples were sparged vigorously with air for three hours at room temperature, then analyzed for phenol content.

| Sample | Additive(s) | % Phenol Removal |
|---|---|---|
| 1 | None | 2.7 |
| 2 | Peroxidase, AO, MeOH | 100 |
| 3 | Peroxidase, AO, MeOH, bacteria | 99.7 |
| 4 | Bacteria | 10.3 |

The results of these experiments demonstrate that the inventive waste water treatment process is effective for removing phenol from a simulated waste stream (See Sample 2). Note that bacteria adapted to growth on lower levels of phenol impurity are relatively ineffective over the time period studied. Further, the combination of enzymatic treatment disclosed herein with bacterial phenol removal is seen to be compatible, such that the inventive method would provide a suitable means to treat surges of waste water impurities.

EXAMPLE XIV

The efficiency of the inventive wastewater treatment process compared to the prior art method was tested as follows. Two 1000 mL beakers were charged with:
- 100 mL of 50 mM potassium phosphate buffer (pH 7.5)
- 1 mL of horseradish peroxidase (100 U/mL)
- 10 μL of water-saturated phenol and either:
- 400 μL of 30% $H_2O_2$ or
- 100 μL methanol plus
- 100 μL of alcohol oxidase (100 U/mL)

Based on the known activity of alcohol oxidase, the methanol-alcohol oxidase combination employed was calculated to be capable of generating the equivalent of 80 μL of 30% $H_2O_2$ at room temperature in one hour. Thus, much larger amounts of $H_2O_2$ were added to the prior art sample than to the system generating $H_2O_2$ in situ. Each solution was stirred at room temperature for one hour, then assayed for disappearance of phenol. The prior art sample (direct addition of $H_2O_2$) gave 50% phenol removal while the inventive treatment (in situ $H_2O_2$ generation) gave essentially quantitative phenol removal over the same time period.

The results of these experiments demonstrate the surprising improvement in the efficiency of removal of aromatic hydroxy compounds by in situ generation of $H_2O_2$ versus direct addition of $H_2O_2$ in the presence of peroxidase enzyme even when the potential $H_2O_2$ concentration of the present invention was much less than the $H_2O_2$ concentration of the prior art (direct addition) method.

EXAMPLE XV

The invention wastewater treatment process was carried out employing peroxidase, glucose oxidase and a suitable substrate. Thus, two 1000 mL beakers were charged as follows:
- 100 mL of 0.02N sodium acetate buffer (pH 5.5)
- 100 U peroxidase (Sigma Chemical Co., Type II)
- 130 U glucose oxidase (Sigma Chemical Co., Type VII)
- 10 μL guaiacol In one beaker, 0.5 g of D-glucose was added as substrate for glucose oxidase, while in the other beaker, 1 g of sucrose and 370 U of invertase (Sigma Chemical Co.) were employed as glucose oxidase substrate. The contents of both beakers were stirred at room temperature for three hours, then monitored for guaiacol removal. In both cases, essentially quantitative guaiacol removal was achieved.

The results of these experiments demonstrate that the inventive wastewater treatment process is operable employing glucose oxidase plus glucose or a glucose precursor for in situ $H_2O_2$ generation.

EXAMPLE XVI

The effect of glucose oxidase concentration on the % removal of aromatic hydroxy compounds was studied. Varying amounts of glucose oxidase (130 U/mL) were added to a series of 1000 mL beakers each containing a standard mixture comprising:
- 100 mL of 20 mM sodium acetate buffer (pH 5.5)
- 1 mL peroxidase (100 U/mL)
- 10 μL of guaiacol
- 0.5 g D-glucose The solutions were stirred for one hour at room temperature before being analyzed by glc for guaiacol removal.

| Sample | μL Added Glucose Oxidase | % Guaiacol Removal |
| --- | --- | --- |
| 1 | 10 | 36 |
| 2 | 25 | 67 |
| 3 | 50 | 100 |
| 4 | 100 | 100 |
| 5 | 250 | 100 |
| 6 | 500 | 100 |
| 7 | 1000 | 100 |

The results of these experiments demonstrate the effectiveness of the inventive process for the removal of aromatic hydroxy compounds such as guaiacol from aqueous solution. Excellent guaiacol removal is achieved with glucose oxidase levels as low as about 50 U per liter of solution to be treated.

EXAMPLE XVII

A further series of runs were carried out to show the effect of in situ generation of $H_2O_2$ on the removal of phenol from artificial waste water. Various methanol concentrations were used such that total oxidation as catalyzed by alcohol oxidase would yield the same amount of $H_2O_2$ as a paired control (where $H_2O_2$ was added directly as per the prior art waste water treatment). Paired 1000 mL beakers were charged with 100 mL of 50 mM potassium phosphate buffer (pH 7.5), 1 mL horseradish peroxidase (100 U/mL), 10 μL phenol and various additives as indicated below. The solutions contained 100 ppm final concentration in phenol. After incubation at room temperature for one hour while being constantly aerated by stirring, the remaining phenol was determined by glc.

| Sample | Additive(s) | Phenol Remaining (ppm) |
| --- | --- | --- |
| 1A | 200 μL MeOH + 200 μL AO (500 U/mL) | 10.4 |
| 1B | 500 μL $H_2O_2$ (30%) | 53.5 |
| 2A | 100 μL MeOH + 200 μL AO | 6.9 |
| 2B | 250 μL $H_2O_2$ (30%) | 47.1 |
| 3A | 50 μL MeOH − 200 μL AO | 9.5 |
| 3B | 125 μL $H_2O_2$ (30%) | 35.7 |
| 4A | 25 μL MeOH + 200 μL AO | 6.7 |
| 4B | 67 μL $H_2O_2$ (30%) | 28.2 |
| 5A | 5 μL MeOH + 200 μL AO | 6.7 |
| 5B | 12 μL $H_2O_2$ (30%) | 25.7 |
| 6A | 10 μL MeOH (10%) + 200 μL AO | 45.1 |
| 6B | 30 μL $H_2O_2$ (3%) | 76.4 |
| 7A | 2.5 μL MeOH (10%) + 200 μL AO | 85.3 |
| 7B | 7.5 μL $H_2O_2$ (3%) | 100.0 |

Comparing the paired Examples 1 through 5 shows that the in situ generation of hydrogen peroxide by the alcohol oxidase—catalyzed oxidation of methanol removes more phenol than that achieved with the prior art system over 40 fold concentration range of methanol. Paired Examples 6 and 7 show that phenol removal of either system is degraded when $H_2O_2$ or 'potential $H_2O_2$' concentration in the reagent solution is less than stoichiometric with the phenol concentration.

The results of these experiments demonstrate the unexpected improvement in the efficiency of removal of aromatic hydroxy compounds by the in situ generation of $H_2O_2$ over a wide range of $H_2O_2$ or 'potential $H_2O_2$' concentrations. The concentrations of phenol remaining after enzyme treatment were about 5 times lower in the in situ procedure compared to a matched prior art sample.

EXAMPLE XVIII

In order to further show the time-course effect, the inventive waste water treatment process was compared with a paired sample using the prior art process (direct addition of H$_2$O$_2$) as follows.

A first 1000 mL beaker (Sample A) was charged with:
100 mL of 50 mM potassium phosphate buffer (pH 7.5)
1 mL of horseradish peroxidase (100 U/mL)
25 μL 30% hydrogen peroxide.

A second 1000 mL beaker (Sample B) was charged with:
100 mL of 50 mM potassium phosphate buffer (pH 7.5)
1 mL of horseradish peroxidase (100 U/mL)
10 μL of methanol
100 μL alcohol oxidase.

The solutions in each beaker containing 100 ppm phenol were incubated at room temperature for up to 6 hours while being constantly stirred for adequate aeration. At selected times, samples were taken from each beaker and phenol remaining was assayed by glc.

| Lapsed Time (hr.) | Phenol Remaining (ppm) | |
|---|---|---|
| | Sample A (Prior Art) | Sample B (Inventive Method) |
| 0.25 | N.D.* | 37.4 |
| 0.5 | N.D. | 8.1 |
| 1.0 | 26.2 | 2.4 |
| 2.0 | 25.7 | 2.4 |
| 3.0 | 25.3 | 2.4 |
| 6.0 | 24.4 | 2.0 |

*Not done.

The results of these experiments demonstrate that the improved effectiveness of the inventive process for the removal of aromatic hydroxy compounds such as phenol from aqueous solution is not limited to the period of incubation. Even prolonged incubation periods of 2 to 6 hours do not lead to the prior art process catching up with the inventive process in terms of effectiveness to lower the concentration of phenol.

EXAMPLE XIX

The use of intact yeast cells containing alcohol oxidase as a substitute for an aqueous solution of alcohol oxidase enzyme was studied. Catalase, which was present in cells containing alcohol oxidase, was inactivated by pretreatment of the cells with 0.02% sodium azide. Were catalase present, it would rapidly break down any H$_2$O$_2$ formed to O$_2$ and H$_2$O. To a series of one liter beakers containing 100 mL of 0.05M potassium phosphate buffer (pH 7.5), 10 μL of water-saturated phenol (100 ppm final concentration) and 100 μL methanol was added with stirring either 100 μL alcohol oxidase (1000 U/mL) or 1 mL of sodium azide-treated yeast cell suspension (estimated to contain 130 mg dry weight yeast and 100 U alcohol oxidase). The mixtures were aerated by stirring for 3 hours at room temperature. The percent removal of phenol was then determined by glc.

As expected, better than 95% of the phenol was removed in the treated solution containing soluble alcohol oxidase. The solution containing alcohol oxidase inside of whole yeast cells removed 64% of the phenol. When cells were used which were not pretreated with sodium azide, essentially no phenol was removed from the artificial waste water.

This Example demonstrates that whole cells containing alcohol oxidase can be used in the inventive process providing that the catalase present in such cells is selectively destroyed. Also, since the alcohol-oxidase containing whole cells are insoluble particles, the cells can be recovered by centrifugation or filtration for further use. Thus, this Example demonstrates the use of an immobilized-form of oxidase in the in situ process for the removal of aromatic hydroxy compounds from waste water.

Reasonable variations and modifications are possible from the foregoing disclosure without departing from the spirit and scope of the present invention.

I claim:

1. A process for the removal by precipitation of at least one compound selected from the group consisting of aromatic hydroxy compounds or aromatic amines having a water solubility of at least about 0.01 mg/l from water containing the same, which comprises treating while aerating at a pH of about 4 to 11 and a temperature in the range of 0° to 50° C. the water containing said compound with peroxidase, alcohol oxidase and a straight chain C$_1$ to C$_4$ alcohol, and wherein the peroxidase, alcohol, and alcohol oxidase are present, respectively, in amounts of from 0.1–10,000 U, 5–10,000 mg, and 0.1–10,000 U per liter of water, thereby precipitating said compound.

2. A process according to claim 1 wherein said alcohol is methanol.

3. A process according to claim 1 wherein (a) said alcohol is ethanol.

4. A process according to claim 1 wherein said water is treated at a pH of from about 6 to about 10.

5. A process according to claim 1 wherein said peroxidase, alcohol, and alcohol oxidase are present, respectively, in amounts of from 10–1000 U, 25–750 mg, and 10–1000 U per liter of water.

6. A process according to claim 1 wherein sodium azide is additionally added during the treating step.

7. A process for the removal by precipitation of at least one compound selected from the group consisting of aromatic hydroxy compounds or aromatic amines having a water solubility of at least about 0.01 mg/l from water containing the same, which comprises treating while aerating at a pH of at least about 4 to 11 and a temperature in the range of 0° to 40° C. the water containing said compound with peroxidase, glucose oxidase and glucose, and wherein the peroxidase, glucose, and glucose oxidase are present, respectively, in amounts of from 0.1–10,000 U, 5–10,000 mg and 0.1–10,000 U per liter of water, thereby precipitating said compound.

8. A process according to claim 7 wherein said peroxidase, glucose, and glucose oxidase are present, respectively, in amounts of from 10–1000 U, 25–750 mg, and 10–1000 U per liter of water.

9. A process according to claim 7 wherein sodium azide is additionally added during the treating step.

10. An enzyme reagent system consisting essentially of (a) peroxidase, (b) one of alcohol oxidase or glucose oxidase, and (c) from 0.01 to 0.05 weight percent of an azide compound of the formula MN$_3$ wherein M is NH$_4^+$ or an alkali metal wherein the ratio of (a) to (b) is 10:1 to 1:10.

11. An enzyme reagent system according to claim 10 wherein (b) is alcohol oxidase and said azide compound (c) is sodium azide.

12. An enzyme reagent system according to claim 10 wherein (b) is glucose oxidase and said azide compound (c) is sodium azide.

13. An enzyme reagent system according to claim 10 wherein said azide compound is sodium azide.

14. An enzyme reagent system according to claim 10 wherein said alcohol oxidase or glucose oxidase is present in an amount in the range of 10 to 1000 Units/mL and said peroxidase is present in an amount in the range of 10 to 10,000 ppg Units/mL.

* * * * *